United States Patent [19]

Hosogane et al.

[11] Patent Number: 5,247,047

[45] Date of Patent: Sep. 21, 1993

[54] METHOD FOR PRODUCING AROMATIC POLYAMIDE OLIGOMERS CONTAINING POLYMERIZABLE UNSATURATED GROUPS AND COMPOSITIONS THEREOF

[75] Inventors: Tadayuki Hosogane, Yokohama; Hiroshi Nakajima, Sawa, both of Japan

[73] Assignee: Showa Highpolymer Co., Ltd., Tokyo, Japan

[21] Appl. No.: 817,637

[22] Filed: Jan. 7, 1992

[30] Foreign Application Priority Data

Jan. 11, 1991 [JP] Japan .................................. 3-014007

[51] Int. Cl.$^5$ .............................................. C08G 18/04
[52] U.S. Cl. ........................................ 528/49; 528/73; 528/75; 525/419; 548/420; 560/225; 564/50; 564/315; 564/305
[58] Field of Search ............................. 528/49, 75, 73; 524/104; 525/419; 548/420; 560/225; 564/50, 315, 305

[56] References Cited

U.S. PATENT DOCUMENTS

| | | | |
|---|---|---|---|
| 4,108,810 | 8/1978 | Baker | 521/129 |
| 4,110,274 | 8/1978 | Corbett et al. | 521/157 |
| 4,187,366 | 2/1980 | Friedlander et al. | 528/75 |
| 4,497,944 | 2/1985 | Nishiyawa et al. | 528/49 |

FOREIGN PATENT DOCUMENTS 2-258868  10/1990  Japan .

*Primary Examiner*—Maurice J. Welsh
*Attorney, Agent, or Firm*—Sughrue, Mion, Zinn, Macpeak & Seas

[57] ABSTRACT

Aromatic polyamide oligomers containing polymerizable unsaturated groups are prepared by heating and reacting together an aromatic diisocyanate, an aromatic dicarboxylic acid and an unsaturated compound capable of reacting with the aromatic diisocyanate. The aromatic polyamide oligomers thus obtained have excellent molding processability and are useful as raw materials for thermosetting polyamides with enhanced mechanical strength and chemical stability at higher temperatures. The compositions comprising the aromatic polyamide oligomers and maleimide derivatives, further produce cured molded bodies with excellent heat resistance.

6 Claims, No Drawings

METHOD FOR PRODUCING AROMATIC POLYAMIDE OLIGOMERS CONTAINING POLYMERIZABLE UNSATURATED GROUPS AND COMPOSITIONS THEREOF

BACKGROUND OF THE INVENTION

Field of the Invention

The present invention relates to a method for producing aromatic polyamide oligomers containing polymerizable unsaturated groups and compositions thereof, from an aromatic diisocyanate, an aromatic dicarboxylic acid, and an unsaturated compound capable of reacting with the aromatic diisocyanate.

More specifically, the present invention relates to a method for producing oligomers useful as materials for heat-resistant synthetic resins, in particular as materials for heat-resistant aromatic polyamides imparted with thermosetting properties, from an aromatic diisocyanate, an aromatic dicarboxylic acid, and an unsaturated compound capable of reacting with the aromatic diisocyanate.

Description of the Related Art

Industrial materials having specific properties are now required as demands from the plastic industry have come more intensive. Such trends have developed rapidly along with the rapid development of the industry.

The demand for improvements in heat resistance has largely arisen because of intentions to enlarge the market and advance into a broad range of new fields with novel functions, by imparting heat resistance to industrial materials in areas requiring heat resistance, such as plastics, film, fibers, laminates, laminated boards and adhesives.

In order to satisfy such requirements a series of synthetic resins called engineering plastics, such as aromatic polyamides, polyimides, polysulfones, polyphenylene oxides, etc., plastics having novel functions differing from those of conventional synthetic resins, have already been developed and industrially produced. Such synthetic resins are now opening up new fields of demand. An aromatic polyamide known as Aramid is one such resin.

Polyparaphenylene terephthalamide (product name: KEVLAR) and polymethaphenylene isophthalamide (product name: Nomex or HT-1), both developed by Du Pont Co. Ltd., are representative types of aromatic polyamide.

All of these types of polyamide are essentially classified as thermoplastic synthetic resins, but they generally have high melting points and in some of them, the difference between the melting point and the thermal decomposition temperature is small or inverted. One drawback of these polyamides, therefore, has been that melt molding thereof was difficult or impossible depending on their respective structures. In contrast, no polyamide has ever been proposed in which an oligomer is prepared as a precursor and subsequently thermoset. The reason why no thermosetting aromatic polyamides have been available is presumably due to the fact that the melting points thereof are generally quite high compared with the melting points of conventional thermosetting synthetic resins, and that the introduction of unsaturated bonds is considered to cause a higher risk of gelation during the molding process.

SUMMARY OF THE INVENTION

Aromatic polyamides are good heat-resistant polymers which are relatively stable at substantially high temperatures and have excellent electric properties and mechanical strength together with chemical stability.

It is the objective of the present invention to develop a material for the preparation of aromatic polyamides having enhanced molding processability without losing the excellent properties of conventional polyamides and having enhanced mechanical strength and chemical stability at high temperatures.

In order to obtain aromatic polyamides having a relatively low melting points, capable of being molded into desirable forms under heated and pressurized conditions, and curable under relatively mild conditions, thereby acquiring satisfactory heat resistance, mechanical strength, chemical stability, etc., for the molding and processing thereof as a molding material or a laminated board, the present inventors have developed a method for producing aromatic polyamide oligomers containing polymerizable unsaturated groups, in which an aromatic diisocyanate, an aromatic dicarboxylic acid and an unsaturated compound capable of reacting with the aromatic diisocyanate in the presence of a solvent are reacted.

According to the method of production of the present invention, unsaturated polyamide oligomers with polymerizable unsaturated groups or alicyclic unsaturated groups at their termini have been produced. These are represented by the following general formulae:

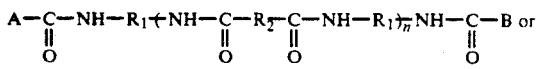 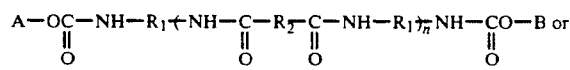

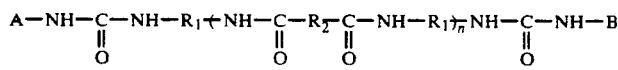 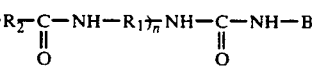

where $R_1$ and $R_2$ each individually represents divalent aromatic groups; A and B represent unsaturated polymerizable groups which may be identical; and n is an arbitrary number from 0 to 15; or

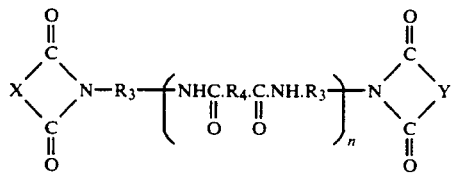

where $R_3$ and $R_4$ each individually represents divalent aromatic groups; X and Y represents unsaturated aliphatic groups which may be identical, and n is an arbitrary number from 0 to 15.

The present inventors have found that these oligomers are curable in the presence of heat or a radical-generating catalyst and the resulting cured aromatic polyamides have the superior properties described above. They have thus achieved the present invention.

The present inventors have also found that, by blending maleimide derivatives of the unsaturated polyamide oligomer described above, curable compositions can be obtained; that the moldability of said compositions is good because the melting points thereof are low; and that aromatic polyamide cured products with less deterioration of mechanical properties and with excellent heat resistance even at higher temperatures can be produced through the curing of these compositions.

DETAILED DESCRIPTION OF THE INVENTION

The present invention will now be explained in detail.

The aromatic polyamide oligomers containing polymerizable unsaturated groups of the present invention can be synthesized according to the following various reactions for example:

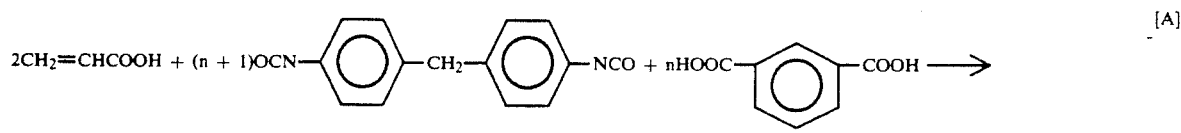
[A]

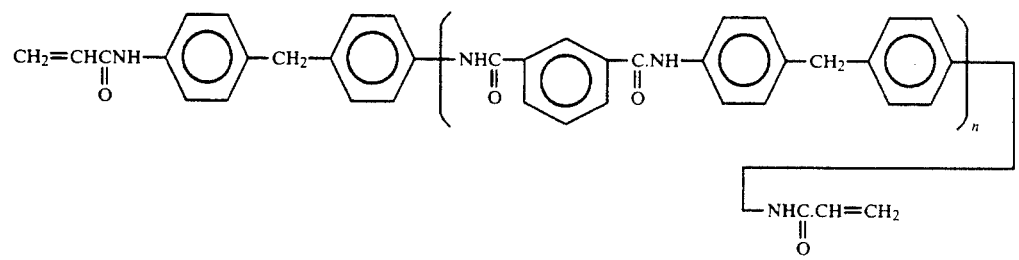

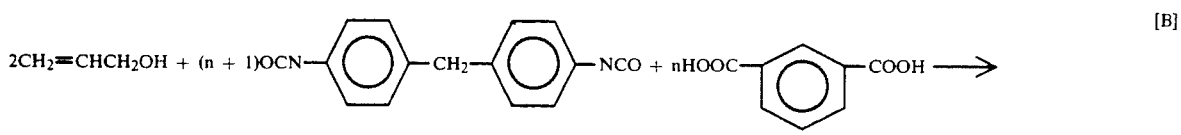
[B]

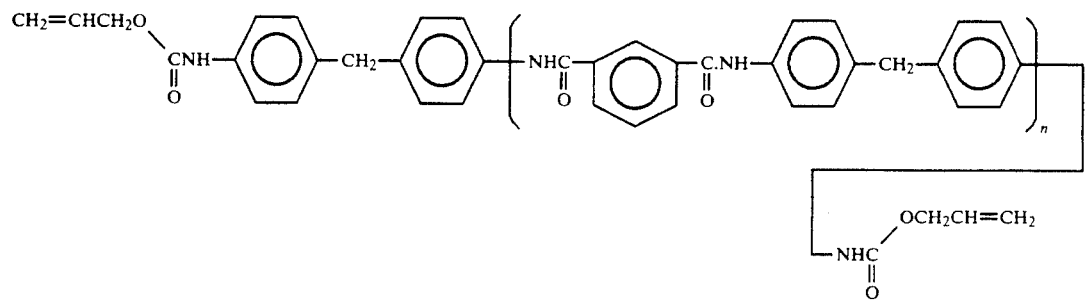

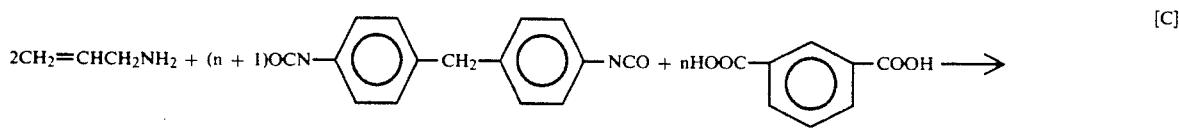
[C]

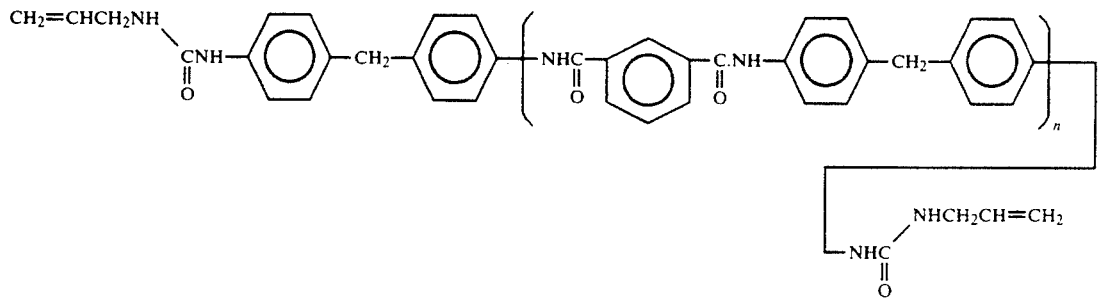

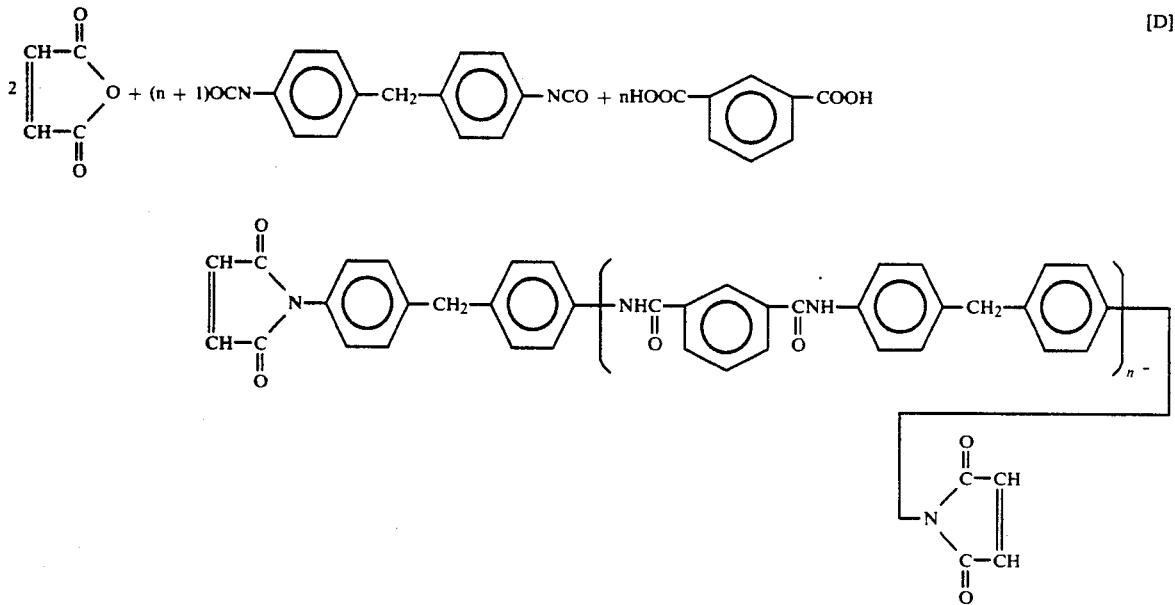

[D]

where an oligomer with a value of n from 0 to 15, preferably about 3 to 7, is advantageous from the viewpoint of easy moldability. Polymerization at this stage is absolutely unnecessary.

For the smooth promotion of the reactions described above, such reactions may be carried out in the presence of a catalyst.

The aromatic diisocyanates usable in the present invention include 2,2-diphenylpropane-4,4'-diisocyanate, diphenylmethane-4,4'-diisocyanate, biphenyl-4,4'-diisocyanate, diphenylsulfide-4,4'-diisocyanate, diphenylsulfone-4,4'-diisocyanate, diphenylether-4,4'-diisocyanate, tolylene-2,4diisocyanate, tolylene-2,6-diisocyanate, and a mixture of tolylene-2,4-diisocyanate and tolylene-2,6-diisocyanate. Of these, it is preferable to use diphenylmethane-4,4'-diisocyanate, tolylene-2,4-diisocyanate or a mixture of tolylene-2,4-diisocyanate and tolylene-2,6-diisocyanate, which are relatively inexpensive, readily available and can also be handled easily on an industrial scale. These isocyanates may be used singly or in combination with each other.

The aromatic dicarboxylic acids usable in the present invention include, for example, terephthalic acid, isophthalic acid, phthalic acid, naphthalene-2,6-dicarboxylic acid or mixtures thereof.

The heat resistance of the aromatic polyamides derived from phthalic acid is slightly deficient; when terephthalic acid is used, the heat resistance of the polymers after thermosetting is satisfactory but the aromatic polyamide oligomers obtained as precursors have higher melting points making them difficult to handle. Thus, in practical terms isophthalic acid has the most balanced properties and satisfies the objectives of the present invention.

The unsaturated compounds capable of reacting with the aromatic diisocyanate which are used in the present invention include unsaturated carboxylic acids, unsaturated amines, unsaturated alcohols and unsaturated alicyclic acid anhydrides.

The unsaturated carboxylic acids include acrylic acid, methacrylic acid, cinnamic acid, crotonic acid, 4-vinylbenzoic acid, or compounds represented by the following formulae:

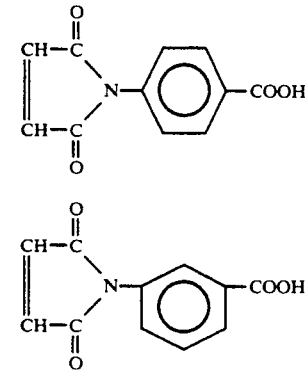

The unsaturated alcohols include allyl alcohol, crotyl alcohol, methylvinyl carbinol, propargyl alcohol, 2-butyn-1-ol, 3-butyn-2-ol, 3-butyn-1-ol, 5-norbornene-2-methanol, cinnamyl alcohol, etc.

The unsaturated amines include allyl amine, diallyl amine, methallyl amine, allylmethyl amine, 1-amino-4-pentene, m-isopropenyl aniline, p-isopropenyl aniline, o-aminostyrene, m-aminostyrene, p-aminostyrene, etc.

The cyclic unsaturated acid anhydrides include maleic anhydride, citraconic anhydride, tetrahydrophthalic anhydride, methyltetrahydrophthalic anhydride, endomethylene tetrahydrophthalic anhydride, methyl endomethylene tetrahydrophthalic anhydride, etc.

Since these synthetic reactions progress comparatively stoichiometrically, the required amounts of the unsaturated carboxylic acid, the aromatic diisocyanate and the aromatic dicarboxylic acid may be reacted after a desirable value for n is inserted into formula [A] above; the required amounts of the unsaturated alcohol, the aromatic diisocyanate and the aromatic dicarboxylic acid may be reacted after a desirable value for n is inserted into formula [B] above; the required amounts of the unsaturated amine, the aromatic diisocyanate and the aromatic dicarboxylic acid may be reacted after a desirable value for n is inserted into formula [C] above; or required amounts of the cyclic unsaturated acid anhydride, the aromatic diisocyanate and the aromatic dicarboxylic acid may be reacted after a desirable value for n is inserted into formula [D] above. If precise adjustment is needed, molar ratios can be determined by simple tests.

The composition of the aromatic polyamide oligomers obtained by these reactions can be easily selected, as has been described above. Furthermore, it is also easy to prepare oligomers moldable at temperatures of 200° C. or less.

The reaction enabling the preparation of aromatic polyamide oligomers containing polymerizable unsaturated groups of the present invention is effected in a homogeneous solution which is prepared from a solvent or a mixture of solvents which can dissolve aromatic diisocyanates, aromatic dicarboxylic acids, unsaturated carboxylic acids, unsaturated alcohols, unsaturated amines, cyclic unsaturated acid anhydrides and the aromatic polyamide oligomers produced. The solvents used are polar solvents, particularly N,N-dimethylacetamide, N,N-dimethylformamide, N-methyl-2-pyrrolidone, dimethyl sulfoxide, 1,1,3,3-tetramethyl urea, 1,3-dimethyl urea or a mixture thereof. In addition, these must be absolutely anhydrous.

Condensation reactions can be effected at temperatures of 50° to 200° C., preferably at 80 to 190° C., in the presence of the polymerization inhibitors for the unsaturated groups of unsaturated carboxylic acids, unsaturated alcohols, unsaturated amines or cyclic unsaturated acid anhydrides. The polymerization inhibitors which can be used include hexaphenyl azobenzene, azobenzene, benzoquinone, toluquinone, zinc- or copper dimethyl dithiocarbamate and triphenyl phosphite.

The amount of any such polymerization inhibitor to be used is generally 0.1 to 2% of the total amount of raw materials used.

In preparing aromatic polyamide oligomers containing polymerizable unsaturated groups in accordance with the present invention, the reaction can be promoted in the presence of known catalysts. The catalysts which can be used include, for example, 1,4-diazabicyclo-[2,2,2]octane, N,N'-dialkyl piperazine, N-alkylmorpholine, dibutyltin dilaurate, cobalt acetylacetonate, metal alkoxide, and alkali metal salts of polyvalent carboxylic acid.

The amount of catalysts to be used is generally 0.01 to 2% of the raw materials used.

The aromatic polyamide oligomers having polymerizable unsaturated groups at their termini synthesized in accordance with the present invention may be cured using radical-generating catalysts or anion-polymerizing catalysts in combination, leading to far greater improvements in heat resistance.

The compositions produced by blending maleimide derivatives with the oligomers produced as described above have improved moldability because the melting points thereof are low. Aromatic polyamide cured products with less deterioration of the mechanical properties even at high temperatures and with excellent heat resistance can be obtained by curing these compositions.

These are three maleimide derivatives which can be used in combination with the aromatic polyamide oligomers in accordance with the present invention.

(1) Phenylmaleimides.
(2) Dimaleimides synthesized from aromatic diamine and maleic anhydride.

The aromatic diamines usable in the present invention include, e.g., m-phenylenediamine, 4,4'-diaminodiphenylmethane, 4,4'-diaminodiphenylpropane, 3,3'-dimethyl-4,4'-diaminodiphenylmethane, 4,4'-diaminodiphenyl ether, 3,4'-diaminodiphenyl ether, 3,3'-diaminodiphenyl sulfone, 4,4'-diaminodiphenyl sulfone, dianisidine, toluylene-2,4-diamine, toluylene-2,6-diamine, and a mixture of toluylene-2,4-diamine and toluylene-2,6-diamine.

(3) Polymaleimides synthesized from polyamines such as aniline-formaldehyde condensate or aniline-terephthalaldehyde condensate and maleic anhydride.

Furthermore, compounds (1), (2) and (3) are also used in combination.

Phenylmaleimides have the lowest melting point and the widest range of compatibility with aromatic polyamide oligomers, but are slightly deficient in heat resistance. Generally, dimaleimides having aromatic diamines as their raw materials can be used.

Examples of these include N-phenylmaleimide, N-(O-chlorophenyl)maleimide, N,N'-diphenylmethane bismaleimide, N,N'-diphenylether bismaleimide, N,N'-paraphenylene bismaleimide, N,N'-(2-methylmethaphenylene)bismaleimide, N,N'-methaphenylene bismaleimide, N,N'-(3,3'-dimethyldiphenylmethane)bismaleimide, N,N'-(3,3'-diphenylsulfone)bismaleimide and maleimides of aniline-formaldehyde condensate (see the following formulas for example)

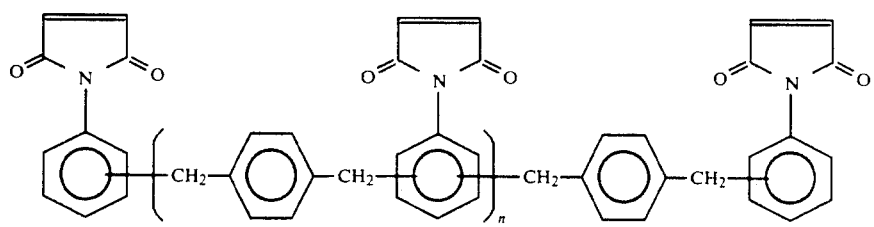

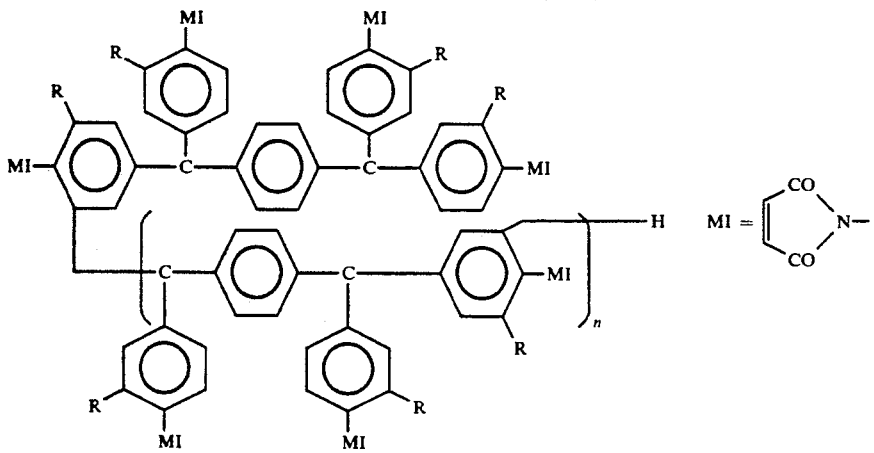

Aromatic polyamide oligomers having polymerizable unsaturated groups at their termini in accordance with the present invention, generally show a slower curing rate, and thus require heating at higher temperatures for a relatively long period even if radical-generating agents are used as catalysts. The curing rate thereof can be improved by blending maleimide derivatives therewith.

Furthermore, by blending with moleimide derivative, a melting point of the composition becomes lower than that of the sole ingredient. As the consequence improved moldability with low molding temperature and pressure can be attained.

The blending ratio is to be 10 to 200 parts by weight of maleimide derivative, preferably 10 to 100 parts to 100 parts by weight of aromatic polyamide oligomer.

There are no specific limitations on the radical generating catalysts, but peroxide types are the most suitable from an industrial viewpoint. If the molding temperature is to be 100° C. or more, catalysts effective at high temperature, e.g., dicumyl peroxide-type catalysts may be used.

The appropriate amount of catalyst to be used is 0.1 to 3 phr.

Combined use with monomers copolymerizable with the unsaturated bond of the oligomers of the present invention is possible when the monomers dissolve the aromatic polyamide oligomers and maleimide derivatives. The range of application is particularly broad when the n of formulae [A], [B], [C], or [D] has a low value. The use of such monomers in combination promotes the softening of the entire condensation system, and improves moldability and workability, but tends to lower the heat resistance of the cured aromatic polyamides. Thus, the addition thereof needs to be adjusted according to the objectives to be met.

In preparing aromatic polyamide oligomers containing polymerizable unsaturated groups in accordance with the present invention, other polymers as low profile additive, reinforcing materials, fillers, releasing agents, colorants, etc. can of course be used in combination as required.

EXAMPLES

The methods of the present invention are illustrated with reference to the following examples, but the invention is not intended to be limited only to these examples.

EXAMPLE 1

Synthesis of polyamide oligomer [I] and curing

A 500-ml separable flask equipped with a stirrer, a thermometer, a reflux condenser, and a nitrogen-introducing tube, was charged with 13.83 g of isophthalic acid, 2.87 g of maleic anhydride, 25 g of diphenylmethane-4,4'-diisocyanate (hereafter "MDI"), 200 g of N,N-dimethylformamide (hereafter "DMF") and 0.01 g of toluquinone. Nitrogen gas was then introduced into the flask under agitation, and the temperature was gradually raised to 110° C.

The reaction was maintained at 110° C. for six hours, then the resulting reaction mixture was cooled to ambient temperature. When the infrared absorption spectrum of the polymer solution thus obtained was measured, no absorption due to the NCO functional group was observed. The polymer solution was gradually added to a vast amount of water under vigorous agitation to precipitate crystals. The crystals deposited were subjected to suction filtration and dried after washing in water. The melting point of the crystals was 210 to 240° C.

One part by weight of polyamide oligomer [I] thus obtained as crystals and one part by weight of dicumyl peroxide (2% acetone solution) were placed in a test tube. The temperature was raised gradually so that the acetone evaporated, then the mixture was dried. After heating at 160° C. for one hour, after-curing was effected at 200° C. for five hours.

The polymer thus obtained was ground in a mortar, and thermogravimetric analysis was then carried out in air at a rate of temperature rise of 10° C/min. The results were as follows:

| | |
|---|---|
| Temperature at 95% weight retention | 432° C. |
| Temperature at 90% weight retention | 461° C. |
| Weight retention at 500° C. | 81.0% |

EXAMPLE 2

Synthesis of polyamide oligomer [II] and curing

The same procedure under the same conditions as in Example 1 was repeated, except that 13.83 g of isophthalic acid, 7.24 g of N-(4-carboxyphenyl)maleimide, 25 g of MDI, 200 g of DMF, and 0.01 g of toluquinone were used.

The melting point of the oligomer obtained was 260° C. or more. The results of thermogravimetric analysis of the polymer were as follows;

| Temperature at 95% weight retention | 375° C. |
|---|---|
| Temperature at 90% weight retention | 419° C. |
| Weight retention at 500° C. | 73.6% |

EXAMPLE 3

Synthesis of polyamide oligomer [III] and curing

The same procedure under the same conditions as in Example 1 was carried out, except that 16.6 g of isophthalic acid, 3.44 g of methacrylic acid, 30 g of MDI, 200 g of DMF and 0.02 g of toluquinone were used.

The melting point of the oligomer obtained was 280° C. or more. The results of thermogravimetric analysis of the polymer were as follows;

| Temperature at 95% weight retention | 408° C. |
|---|---|
| Temperature at 90% weight retention | 441° C. |
| Weight retention at 500° C. | 78.1% |

EXAMPLE 4

Synthesis of polyamide oligomer [IV] and curing

The same procedure under the same conditions as in Example 1 was repeated, except that 16.6 g of isophthalic acid, 3.44 g of methacrylic acid, 20.88 g of tolylene-2,4-diisocyanate, 150 g of N-methylpyrrolidone, 0.01 g of toluquinone, and 0.02 g of dibutyltin dilaurate were used and that the temperature was raised gradually in a nitrogen stream, followed by reaction at 110° C. for one hour and at 140 to 145° C. for five hours.

The melting point of the oligomer obtained was 220 to 260° C. The results of thermogravimetric analysis of the polymer were as follows;

| Temperature at 95% weight retention | 438° C. |
|---|---|
| Temperature at 90% weight retention | 459° C. |
| Weight retention at 500° C. | 81.8% |

EXAMPLE 5

Synthesis of polyamide oligomer [V] and curing

The same procedure under the same conditions as in Example 4 was repeated, except that 14.94 g of isophthalic acid, 17.40 g of mixed tolylene diisocyanate (mixing ratio of 2,4-/2,6-tolylene diisocyanate = 80/20), 1.44 g of acrylic acid, 200 g of DMF, 0.01 g of toluquinone, and dibutyltin dilaurate were used.

The melting point of the oligomer obtained was 205 to 220 ° C. The results of thermogravimetric analysis of the polymer were as follows;

| Temperature at 95% weight retention | 432° C. |
|---|---|
| Temperature at 90% weight retention | 461° C. |
| Weight retention at 500° C. | 84.5% |

EXAMPLE 6

Synthesis of polyamide oligomer [VI] and curing

The same procedure under the same conditions as in Example 4 was carried out, except that 8.3 g of isophthalic acid, 17.4 g of mixed tolylene diisocyanate (mixing ratio of 2,4-/2,6-tolylene diisocyanate = 80/20), 8.6 g of crotonic acid, 200 g of DMF, 0.01 g of toluquinone and 0.02 g of dibutyltin dilaurate were used.

The melting point of the oligomer obtained was 170° to 185° C. The results of thermogravimetric analysis of the polymer were as follows;

| Temperature at 95% weight retention | 342° C. |
|---|---|
| Temperature at 90% weight retention | 419° C. |
| Weight retention at 500° C. | 71.0% |

EXAMPLE 7

Synthesis of polyamide oligomer [VII] and curing

The same procedure under the same conditions as in Example 4 was carried out, except that 16.6 g of isophthalic acid, 20.88 g of mixed tolylene diisocyanate (mixing ratio of 2,4-/2,6-tolylene diisocyanate = 80/20), 2.32 g of allyl alcohol, 150 g of N-methylpyrrolidone, 0.01g of toluquinone and 0.02 g of dibutyltin dilaurate were used.

The melting point of the oligomer obtained was 260° C. or more. The results of thermogravimetric analysis of the polymer were as follows;

| Temperature at 95% weight retention | 432° C. |
|---|---|
| Temperature at 90% weight retention | 465° C. |
| Weight retention at 500° C. | 84.9% |

EXAMPLE 8

Synthesis of polyamide oligomer [VIII] and curing

The same procedure under the same conditions as in Example 4 was repeated, except that 16.6 g of isophthalic acid, 20.88 g of mixed tolylene diisocyanate (mixing ratio of 2,4-/2,6-tolylene diisocyanate = 80/20), 2.28 g of allyl amine, 150 g of N-methylpyrrolidone, 0.01 g of toluquinone and 0.02 g of dibutyltin dilaurate were used.

The melting point of the oligomer obtained was 260° C. or more. The results of thermogravimetric analysis of the polymer were as follows;

| Temperature at 95% weight retention | 444° C. |
|---|---|
| Temperature at 90% weight retention | 468° C. |
| Weight retention at 500° C. | 85.0% |

EXAMPLE 9

Curing of maleimide compound

One part by weight of polyamide oligomer [I] synthesized in Example 1, 0.15 parts by weight of N-phenylmaleimide, and 1.15 parts by weight of 2% solution of dicumyl peroxide in acetone were placed in a test tube and mixed homogeneously.

The temperature was increased gradually, and the resulting mixture was heated at 80° C. for one hour to evaporate the acetone, and then dried. After drying, the temperature was increased to 160° C. and the mixture cured for two hours. The temperature was increased further to 200° C., and five-hour after curing was subsequently effected. A polymer in a rigid, insoluble, infusible amber-colored mass was obtained.

The polymer thus obtained was ground in a mortar, and a thermogravimetric analysis was then carried out in air at a rate of temperature rise of 10° C./min. The results are shown as follows.

| Temperature at 95% weight retention | 342° C. |
|---|---|
| Temperature at 90% weight retention | 402° C. |
| Weight retention at 500° C. | 71.6% |

EXAMPLE 10 TO 18

The same procedure as in Example 1 was performed with the formulations described in Table 1. The results of thermogravimetric analysis are shown in Table 1.

N,N'-diphenylmethane bismaleimide and oligomer [IV] obtained in Example 4 are shown in Table 2.

TABLE 2

| | | | | |
|---|---|---|---|---|
| Oligomer [IV] from Example 4 | 100 parts | 100 parts | 100 parts | 100 parts |
| N-phenylmaleimide | — | 20 parts | 100 parts | — |
| N,N'-diphenylmethane bismaleimide | — | — | — | 100 parts |
| Melting point | 210 to 250° C. | 110 to 140° C. | 90 to 140° C. | 150 to 190° C. |

Since conventional aromatic polyamides are thermoplastic resins with high melting points, they have drawbacks in terms of moldability, despite their excellent chemical and electrical resistance. In addition, their

TABLE 1

| | Example | | | | | | | | |
|---|---|---|---|---|---|---|---|---|---|
| | 10 | 11 | 12 | 13 | 14 | 15 | 16 | 17 | 18 |
| Polyamide oligomer | | | | | | | | | |
| [I] | 1 | 1 | | | | | | | |
| [II] | | | 1 | | | | | | |
| [III] | | | | 1 | | | | | |
| [IV] | | | | | 1 | | | | |
| [V] | | | | | | 1 | | | |
| [VI] | | | | | | | 1 | | |
| [VII] | | | | | | | | 1 | |
| [VIII] | | | | | | | | | 1 |
| N-phenylmaleimide | 1 | | | | | | | | |
| N,N'-diphenylmethane bismaleimide | | 1 | 1 | 1 | 1 | 1 | 1 | 1 | 1 |
| dicumyl peroxide (2% solution in acetone) | 2 | 2 | 2 | 2 | 2 | 2 | 2 | 2 | 2 |
| Temperature at 95% weight Retention (°C.) | 309 | 417 | 404 | 414 | 414 | 377 | 388 | 414 | 434 |
| Temperature at 90% weight Retention (°C.) | 348 | 441 | 428 | 443 | 438 | 415 | 421 | 438 | 459 |
| Weight retention at 500° C. | 67.8 | 79.2 | 73.1 | 78.0 | 77.0 | 73.2 | 75.3 | 76.8 | 81.4 |

Note: Numerals in formulations denote parts by weight.

EXAMPLE 19

After a piece of glass fabric [manufactured by Nittobo, Co., Ltd. (WEA 05E 106 BY54)] was impregnated with a solution prepared by dissolving 90 parts by weight of oligomer [IV] synthesized in Example 4, 90 parts of N,N'-diphenylmethane bismaleimide and 3 parts of dicumyl peroxide in 220 parts of N-methylpyrrolidone, the fabric was dried at 100° C. for one hour to prepare a prepreg. Thirty sheets of the prepreg were subsequently layed one on top of another and, after heating and pressurizing to 20 kg/cm$^2$ at 160° C. for 15 minutes, after-curing was effected at 200° C. for 48 hours to obtain a laminated board.

The bending strength of the laminated board was 53 kg/mm$^2$ at 25° C., and 45 kg/mm$^2$ at 200° C. The bending strength thereof after heating at 200° C. for 960 hours was 57 kg/mm$^2$ at 25° C.; the bending strength thereof after heating at 250° C. for 960 hours was 44 kg/mm2 at 25° C.; and the bending strength thereof after heating at 300° C. for 24 hours was 50 kg/mm$^2$ at 25° C.

REFERENCE EXAMPLE 1

The compositions produced by adding maleimide derivatives to the aromatic polyamide oligomers show remarkably low melting points, and the processing thereof is easier.

As an example, the melting points of compounds containing various ratios of N-phenylmaleimide or mechanical strengths at higher temperatures deteriorate substantially. Even at temperatures below their melting points or decomposition temperatures, therefore, they have been limited in terms of fields of use.

The present invention has overcome these defects, and has succeeded in developing aromatic polyamide oligomers, having novel unsaturated groups, applicable as raw materials for thermosetting aromatic polyamides with excellent moldability and less deterioration of mechanical strength at high temperatures, even though aromatic polyamide oligomers of the present invention belongs to the same aromatic polyamide group as do conventional aromatic polyamides.

The oligomers are relatively stable exhibiting no gelation during molding, despite having polymerizable double bonds, and have such excellent properties that they can be cured at lower temperatures through combined use with a radical-generating catalyst or an anion-type polymerizable catalyst.

The aromatic polyamides produced by curing the compositions composed of the oligomers or the compositions composed of the oligomers and maleimide derivatives, are aromatic polyamides with excellent heat resistance and in which deterioration of mechanical strength does not occur even at higher temperatures.

What is claimed is:

1. A method for preparing an aromatic polyamide oligomer containing a polymerizable unsaturated group, comprising heating and reacting together (a) an aromatic diisocyanate, (b) an aromatic dicarboxylic acid and (c) an unsaturated compound capable of reacting with the aromatic diisocyanate which unsaturated compound is selected from the group consisting of a polymerizable unsaturated carboxylic acid, an unsaturated amine, and a cyclic unsaturated acid anhydride, in a polar solvent, the aromatic diisocyanate being present in a stoichiometric amount against total functional groups of the aromatic dicarboxylic acid and the unsaturated compound.

2. A method for preparing the aromatic polyamide oligomer as in claim 1, wherein said aromatic diisocyanate is selected from the group consisting of diphenylmethane-4,4'-diisocyanate, tolylenediisocyanate and mixed tolylene diisocyanate; said aromatic dicarboxylic acid is isophthalic acid; and said unsaturated compound capable of reacting with the aromatic diisocyanate is selected from the group consisting of maleic acid, maleic anhydride, acrylic acid, methacrylic acid, crotonic acid, and allylamine.

3. A thermosetting resin composition comprising an aromatic polyamide oligomer containing polymerizable unsaturated groups synthesized by the method claimed in claim 1 and 5 wt% or less of a radical polymerization initiating agent.

4. A thermosetting resin composition produced by blending a maleimide compound with an aromatic polyamide oligomer containing a polymerizable unsaturated group synthesized by heating and reacting together (a) an aromatic diisocyanate, (b) an aromatic dicarboxylic acid and (c) an unsaturated compound capable of reacting with the aromatic diisocyanate which unsaturated compound is selected from the group consisting of a polymerizable unsaturated carboxylic acid, an unsaturated amine, and a cyclic unsaturated acid anhydride in a polar solvent, the aromatic diisocyanate being present in a stoichiometric amount against total functional groups of the aromatic dicarboxylic acid and the unsaturated compound.

5. A thermosetting resin composition as in claim 4, wherein 10 to 200 parts by weight of a maleimide compound are blended with 100 parts by weight of the aromatic polyamide oligomer composition.

6. A thermosetting resin composition as in claim 4, wherein the maleimide compound is selected from the group consisting of a phenylmaleimide, an aromatic dimaleimide and an aromatic polymaleimide.

* * * * *